United States Patent [19]

Turner et al.

[11] Patent Number: 5,186,735
[45] Date of Patent: Feb. 16, 1993

[54] DERIVATIVES OF 4-((ARYLOXY)PHENOXY)ALKENOLS AND THEIR HERBICIDAL USES

[75] Inventors: James A. Turner, Pittsburg; Paul S. Zorner, Clayton; Wendy S. Jacks, Walnut Creek, all of Calif.

[73] Assignee: DowElanco, Indianapolis, Ind.

[21] Appl. No.: 684,701

[22] Filed: Apr. 12, 1991

Related U.S. Application Data

[60] Division of Ser. No. 367,274, Jun. 16, 1989, Pat. No. 5,034,050, which is a continuation of Ser. No. 150,803, Feb. 1, 1988, abandoned, which is a continuation of Ser. No. 837,229, Mar. 7, 1986, Pat. No. 4,731,108.

[51] Int. Cl.$^5$ .................. C07D 239/10; A01N 43/48
[52] U.S. Cl. ..................................... 504/242; 544/318
[58] Field of Search ............................. 544/318; 71/92

[56] References Cited

U.S. PATENT DOCUMENTS

| 4,302,242 | 11/1981 | Cartwright | 71/94 |
| 4,401,460 | 8/1983 | Cartwright et al. | 71/94 |
| 4,427,437 | 1/1984 | Serban et al. | 544/318 |
| 4,508,907 | 4/1985 | Cartwright | 546/345 |
| 4,586,953 | 5/1986 | Cartwright | 71/94 |

FOREIGN PATENT DOCUMENTS

| 0218321 | 4/1987 | European Pat. Off. | |
| 0017303 | 2/1980 | Japan | 544/318 |

Primary Examiner—Mukund J. Shah
Assistant Examiner—Y. N. Gupta
Attorney, Agent, or Firm—S. Preston Jones

[57] ABSTRACT

Derivatives of 4-((aryloxy)phenoxy)alkenols, their preparation and use as active herbicides for the postemergent control of grassy weeds and especially the control of said weeds in the presence of corn plants are disclosed.

13 Claims, No Drawings

DERIVATIVES OF 4-((ARYLOXY)PHENOXY)ALKENOLS AND THEIR HERBICIDAL USES

This is a divisional of application Ser. No. 07/367,274, filed Jun. 16, 1989, now U.S. Pat. No. 5,034,050, which in turn is a continuation of application Ser. No. 150,803, filed Feb. 1, 1988, now abandoned, which in turn is a continuation of application Ser. No. 837,229, filed Mar. 7, 1986, now U.S. Pat. No. 4,731,108.

BACKGROUND OF THE INVENTION

Highly active herbicidal compounds of the class constituting aryloxyphenoxyalkanoic, and aryloxyphenoxyalkenoic acids and related compounds have been described in the patent literature. These compounds have been prepared by making derivatives of the acid function thereof and bearing various groups or substituents on, primarily, the aryl structure. Such compounds in which the aryloxy and O-alkanoic acid functions respectively are disposed in 1,4 relation on the phenyl group, are especially active against grassy, i.e., gramineous weeds while displaying little or no herbicidal activity against broadleaf plants and, often, slight activity against cereal grains. However, these compounds as a group are generally injurious to corn, i.e., maize, and are of little use for controlling grassy weeds in corn crops.

FIELD OF THE INVENTION

The present invention relates to novel highly active herbicidal compounds, compositions containing said compound and methods for the postemergent use thereof in the control of grassy weeds, especially in the presence of grass crops such as corn. The invention relates especially to novel derivatives of 4-((aryloxy)phenoxy)alkenol compositions containing said compounds and the postemergent herbicidal use thereof.

SUMMARY OF THE INVENTION

It has now been discovered that esters of aryloxyphenoxyalkenols, particularly the pentenols, are highly active herbicidal compounds effective in the postemergent, systemic kill or control of grassy weeds while exhibiting little herbicidal action against corn.

The active derivatives of aryloxyphenoxyalkenols of the present invention correspond to the formula

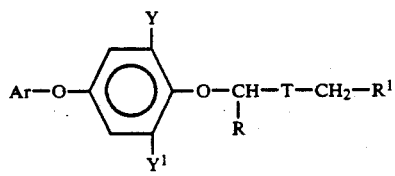

wherein Ar represents

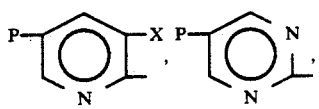

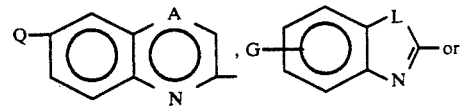

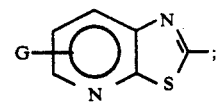

Y and $Y^1$ each independently represent —H or —F;
X represents —H, —Br or —Cl;
R represents methyl or ethyl;
T represents

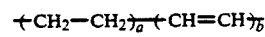

and the cis (Z) or trans (E) stereoisomers thereof or

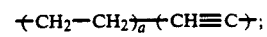

A represents ≡N or ≡CH;
G represents in the 5 or 6 ring position, —Br, —Cl, —F or —CF$_3$;
a represents the integer 0, 1 or 2;
b represents the integer 1 or 2;
P represents —Br, —Cl, —I or —CF$_3$;
Q represents —Br, —Cl, —F or —CF$_3$;
$R^1$ represents —OSO$_2$R$^2$,

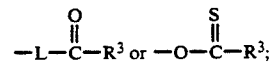

$R^2$ represents $C_1$–$C_4$ alkyl, $C_2$–$C_4$ alkenyl or —NR$^4$R$^5$;
$R^3$ represents $C_2$–$C_4$ alkenyl, $C_1$–$C_4$ alkyl, —NR$^4$R$^5$ or

wherein
$R^4$ and $R^5$ each independently represent —H or $C_1$–$C_4$ alkyl;
D represents $C_1$–$C_4$-alkyl, —Br, —Cl, —NO$_2$, —CF$_3$, —OCF$_3$,

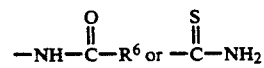

wherein $R^6$ represents $C_1$–$C_4$ alkyl and m represents an integer of from 0–3, inclusive.

The present invention also encompasses compositions containing one or more of these active compounds as well as methods of using such compounds or compositions in the control of grassy weeds, particularly in the presence of corn.

The active compounds of the present invention, hereinafter referred to as "active compounds" or "active ingredients", have been found to be useful as herbicides for the postemergent kill and control of undesirable vegetation, for example, grassy or graminaceous weeds in the presence of corn plants.

The term "herbicide" is used herein to mean an active ingredient which controls or adversely modifies the growth of plants because of phytotoxic or other effects substantial enough to seriously retard the growth of the plant or further to damage the plant sufficiently to kill the plant.

The terms "growth controlling" or "herbicidally effective" amount are employed to designate an amount of active ingredient which causes a modifying effect and includes deviations from natural development, killing, regulation, dessication, retardation, and the like.

The term "plants" means established vegetation.

The terms "control" or "controlling" as it relates to plant growth has the same meaning as employed hereinabove for the term "herbicide".

The term "$C_1$–$C_4$ alkyl" as employed in the present specification and claims designates alkyl groups which can be straight or branched chain containing from 1 to 4 carbon atoms or cycloalkyl of 3 or 4 carbon atoms.

In the present invention, it is to be noted that all substituent groups are sterically compatible with each other. The term "sterically compatible" is employed to designate substituent groups which are not affected by steric hindrance as defined in "The Condensed Chemical Dictionary", 7th edition, Reinhold Publishing Co., N.Y., page 893 (1966) which definition is as follows:

"steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd edition, McGraw-Hill Book Company, N.Y., page 215 (1964).

The active compounds of the present invention contain the optically active center

and can exist in optically active stereoisomeric forms such as the R and S enantiomeric forms. The use of the various mixtures and racemates of the above isomers are within the scope of the present invention. Additionally, the R enantiomer of such compounds have been found to be more active biologically than the S enantiomer and may be used whenever the greater activity justifies the extra expenses for the use of this isomer.

A general discussion of the isomer activity difference phenomenon can be found in A. Albert, Selective Toxicity, 4th edition, Met Luen & Co., Ltd., London, 1968, pp. 387–390 and more particular discussions in A. Fredga and B. Aberg, "Stereoisomerism in plant growth regulators of the auxin type", Ann. Rev. Plant Physiology 16:53–72, 1965, and in E. J. Lien, J. F. R. DeMiranda and E. J. Airens, "Quantitative structure-activity correlation of optical isomers", Molecular Pharmacology 12:598–604, 1976.

The active compounds or ingredients of the present invention are generally oils or low melting crystalline solids at ambient temperatures which are soluble in many organic solvents commonly employed as herbicidal carriers.

Representative active compounds of the present invention are set forth below in Tables 1, 2, 3, 4 and 5.

TABLE 1

![structure]

| P | X | Y | $Y^1$ | R | T | $R^1$ |
|---|---|---|---|---|---|---|
| —Br | —Cl | —H | —H | —$CH_3$ | —CH=CH— | —OC(O)$CH_3$ |
| —Cl | —Cl | —H | —H | —$CH_3$ | —CH=CH— | —OC(O)-n-$C_4H_9$ |
| —$CF_3$ | —Cl | —H | —H | —$CH_3$ | —CH=CH— | —$OSO_2$CH($CH_3$)$_2$ |
| —Br | —Cl | —H | —H | —$C_2H_5$ | +($CH_2CH_2$)(CH—CH)+ | —OC(S)$CH_3$ |
| -I | —Br | —F | —F | —$C_2H_5$ | +CH=CH+ | —OC(O)$C_2H_5$ |
| —$CF_3$ | —Br | —F | —H | —$CH_3$ | —CH=CH— | —OC(O)$CH_3$ |
| -I | —Cl | —F | —F | —$CH_3$ | +CH=CH+ | —$OSO_2CH_3$ |
| —$CF_3$ | —Cl | —H | —H | —$CH_3$ | —CH=CH— | —$OSO_2CH_3$ |
| —$CF_3$ | —Cl | —H | —H | —$C_2H_5$ | —CH=CH— | —OC(S)$CH_3$ |
| —Cl | —Cl | —H | —H | —$CH_3$ | —CH=CH— | —OC(O)N($CH_3$)$_2$ |
| —$CF_3$ | —Cl | —F | —F | —$CH_3$ | —CH=CH— | —OC(O)NH$CH_3$ |
| —$CF_3$ | —Br | —H | —H | —$CH_3$ | —CH=CH— | —OC(O)NH-n-$C_4H_9$ |
| —Cl | —Cl | —H | —H | —$CH_3$ | +CH=CH+ | —$OSO_2$NH$C_2H_5$ |
| —$CF_3$ | —Cl | —H | —H | —$CH_3$ | —CH=CH— | —$OSO_2$CH($CH_3$)$_2$ |
| -I | —Br | —H | —H | —$C_2H_5$ | —$CH_2CH_2$—CH=CH | —$OSO_2C_3H_7$ |
| —Cl | —Cl | —H | —H | —$CH_3$ | —CH=CH— | —OC(S)N($CH_3$)$_2$ |
| —$CF_3$ | —Br | —H | —H | —$CH_3$ | —CH=CH— | 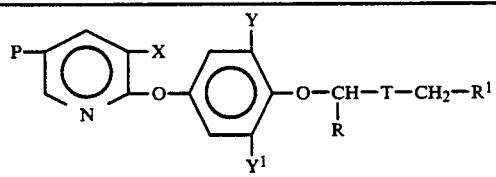 —$OSO_2$—⟨phenyl⟩—$CH_3$ |
| —Br | —Br | —H | —H | —$CH_3$ | —CH=CH— | —OC(O)CH=$CH_2$ |
| -I | —Br | —F | —H | —$CH_3$ | —CH=CH— | —OC(O)N($CH_3$)$C_2H_5$ |

TABLE 1-continued

Structure: P-pyridine(X)-O-phenyl(Y,Y¹)-O-CH(R)-T-CH₂-R¹

| P | X | Y | Y¹ | R | T | R¹ |
|---|---|---|----|----|---|----|
| —CF₃ | —Cl | —H | —H | —CH₃ | —CH=CH— | —OSO₂NHCH(CH₃)₂ |
| —Cl | —Cl | —H | —H | —CH₃ | —CH=CH— | —OC(O)-C₆H₄-OCF₃ |
| —Cl | —Cl | —H | —H | —CH₃ | —CH=CH— | —OC(O)-C₆H₄-Br |
| —Br | —Br | —H | —H | —CH₃ | —CH=CH— | —OC(O)NHC₂H₅ |
| —CF₃ | —Cl | —H | —H | —CH₃ | —CH—CH— | —OC(O)-C₆H₅ |

TABLE 2

Structure: P-pyrimidine-O-phenyl(Y,Y¹)-O-CH(R)-T-CH₂-R¹

| P | Y | Y¹ | R | T | R¹ |
|---|---|----|----|---|----|
| —CF₃ | —H | —H | —CH₃ | —CH=CH— | —OC(O)CH₃ |
| —I | —F | —F | —CH₃ | —CH=CH— | —OC(O)NHCH₃ |
| —CF₃ | —H | —H | —CH₃ | —C≡C— | —OC(O)CH₃ |

TABLE 2-continued

| P | Y | Y¹ | R | T | R¹ |
|---|---|----|----|---|----|
| —I | —H | —H | —CH₃ | —CH=CH— | —OSO₂C(CH₃)₂ |
| —Br | —H | —H | —CH₃ | ∔CH=CH∔₂ | —OSO₂C(CH₃)₂ |

TABLE 3

Structure: Q-quinoxaline(A)-O-phenyl(Y,Y¹)-O-CH(R)-T-CH₂-R¹

| A | Q | Y | Y¹ | R | T | R¹ |
|---|---|---|----|----|---|----|
| ≡CH | —F | —H | —H | —C₂H₅ | ∔CH=CH∔₂ | —OC(O)C₂H₅ |
| ≡N | —Cl | —H | —H | —CH₃ | —CH=CH— | —OC(O)CH₃ |
| ≡N | —Cl | —H | —H | —CH | —CH=CH— | —OC(O)NHCH₃ |
| ≡N | —Cl | —H | —H | —CH₃ | —CH=CH— | —OC(O)-C₆H₅ |
| ≡CH | —Br | —H | —H | —CH₃ | —CH=CH— | —OC(O)CH(CH₃)₂ |
| ≡N | —Cl | —H | —H | CH₃ | —CH=CH— | —OC(O)-C₆H₃Cl₂ (2,6-dichloro) |

TABLE 3-continued

Structure: Q-substituted bicyclic ring system with A in ring, linked via O to a phenyl bearing Y and Y¹, then O—CH(R)—T—CH₂—R¹

| A | Q | Y | Y¹ | R | T | R¹ |
|---|---|---|----|---|---|-----|
| ≡N | —Cl | —H | —H | —CH₃ | —CH=CH— | —OSO₂CH(CH₃)₂ |
| ≡N | —Cl | —H | —H | —CH₃ | —CH=CH— | —OSO₂NHCH(CH₃)₂ |
| ≡N | —Cl | —H | —H | —CH₃ | —CH=CH— | —OC(O)—C₆H₄—C(O)NH₂ |
| ≡N | —Cl | —H | —H | —CH₃ | —CH=CH— | —OC(O)C(CH₃)₃ |
| ≡N | —Cl | —H | —H | —CH₃ | —CH=CH— | —OC(O)—C₆H₄—CF₃ |
| ≡CH | —CF₃ | —H | —H | —C₂H₅ | (CH=CH)₂ | —OC(O)N(CH₃)₂ |
| ≡N | —Cl | —H | —H | —CH₃ | —CH=CH— | —OC(O)—C₆H₄—Cl |
| ≡N | —Cl | —H | —H | —CH₃ | —CH=CH— | —OC(O)—(3-Cl-C₆H₃)— |
| ≡N | —Cl | —H | —H | —CH₃ | —CH=CH— | —OC(O)—C₆H₄—Cl |
| ≡N | —Cl | —H | —H | —CH₃ | —CH=CH— | —OSO₂CH₃ |
| ≡CH | —Cl | —F | —F | —C₂H₅ | (CH₂CH₂)₂(CH—CH₃)₂ | —OC(S)CH₃ |
| ≡N | —Cl | —H | —H | —CH₃ | —CH=CH— | —OC(O)—C₆H₄—NHC(O)CH₃ |
| ≡N | —Cl | —H | —H | —CH₃ | —CH=CH— | —OC(O)C₃H₇ |
| ≡N | —Cl | —H | —H | —CH₃ | —CH=CH— | —OSO₂-n-C₄H₉ |
| ≡N | —Cl | —H | —H | —CH₃ | —CH=CH— | —OSO₂C₃H₇ |
| ≡N | —Cl | —H | —H | —CH₃ | —CH=CH— | —OSO₂C₂H₅ |
| ≡CH | —Cl | —H | —H | —CH₃ | —CH=CH— | —OSO₂CH(CH₃)₂ |
| ≡N | —Cl | —H | —H | —CH₃ | —CH=CH— | —OC(O)—C₆H₄—OCF₃ |
| ≡CH | —Cl | —H | —H | —CH₃ | —CH=CH— | —OC(O)—C₆H₄—OCF₃ |

TABLE 3-continued

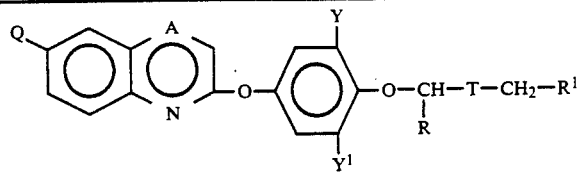

| A | Q | Y | Y¹ | R | T | R¹ |
|---|---|---|----|---|---|-----|
| ≡CH | —Cl | —H | —H | —CH₃ | —CH=CH— | —OC(O)—C₆H₄—CF₃ |
| ≡N | —Cl | —H | —H | —CH₃ | —CH=CH— | —OC(O)—C₆H₄—C₂H₅ |
| ≡N | —Cl | —H | —H | —CH₃ | —CH=CH— | —OC(O)—C₆H₄—NO₂ |
| ≡N | —Cl | —H | —H | —CH₃ | —CH=CH— | —OC(O)—C₆H₄—CH₃ |

TABLE 4

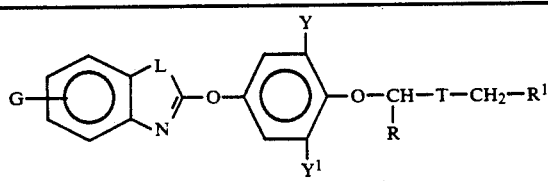

| G | L | Y | Y¹ | R | T | R¹ |
|---|---|---|----|---|---|-----|
| -6-CF₃ | S | —F | —F | —CH₃ | —CH=CH— | —OC(O)C₂H₅ |
| -6-Cl | S | —H | —H | —CH₃ | —CH=CH— | —OC(O)CH₃ |
| -6-Br | S | —F | —H | —CH₃ | —CH=CH— | —OC(O)CH₃ |
| -6-F | S | —H | —H | —CH₃ | —CH=CH— | —OC(O)CH₃ |
| -6-Cl | O | —H | —H | —CH₃ | —CH₂CH₂—CH=CH— | —OC(O)CH₃ |
| -5-Cl | O | —H | —F | —CH₃ | —CH=CH— | —OC(O)CH₃ |

TABLE 5

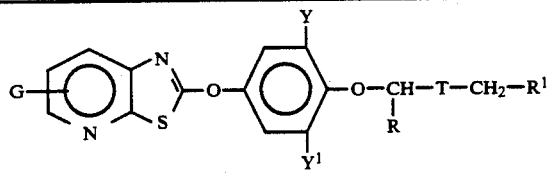

| G | Y | Y¹ | R | T | R¹ |
|---|---|----|---|---|-----|
| -6-CF₃ | —H | —H | —C₂H₅ | (—CH=CH—)₂ | —OC(O)-n-C₄H₉ |
| -6-Cl | —H | —H | —CH₃ | —CH=CH— | —OC(O)—C₆H₅ |
| -5-CF₃ | —F | —F | —CH₃ | —CH=CH | —OC(O)CH₃ |
| -6-Cl | —H | —H | —CH₃ | —CH=CH— | —OC(O)CH₃ |

TABLE 5-continued

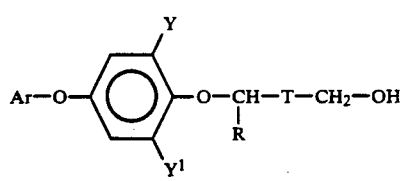

| G | Y | Y¹ | R | T | R¹ |
|---|---|----|---|---|----|
| -6-Cl | —H | —H | —CH$_3$ | —CH=CH— | —OSO$_2$CH(CH$_3$)$_2$ |

The preferred compounds of the present invention include those compounds of Formula I wherein Ar is as follows:
5-chloro-2-pyridyl
5-trifluoromethyl-2-pyridyl
3,5-dichloro-2-pyridyl
5-chloro-5-trifluoromethyl-2-pyridyl
5-chloro-3-fluoro-2-pyridyl
6-chloro-2-quinolinyl
6fluoro-2-quinolinyl
6-chloro-2-quinoxalinyl
6-fluoro-2-quinoxalinyl
6-chloro-2-benzothiazolyl
5-chloro-2-benzoxazolyl
5 -chloro-2-thiazolopyridyl
5-fluoro-2-thiazolopyridyl.

These above compounds are even more preferred when R is methyl, Y and Y¹ are hydrogen, a is 0 and b is 1.

The active ingredients of Formula I wherein R¹ is —OSO$_2$R² constitute a preferred embodiment and active ingredients wherein R¹ is —O—C(O)R³ constitute a further preferred embodiment.

The active ingredients of the above Formula I can be prepared in accordance with one or more of the following procedures.

The compounds of the present invention wherein R¹ is

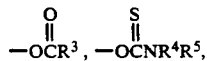

or —OSO$_2$R² where R² and R³ are other than —NHR⁵ and R⁴ is other than hydrogen can be prepared by the condensation of an appropriate 4-((aryloxy)phenoxy)alkenol corresponding to the formula (II)

with an appropriate halide corresponding to the formula

Hal-R⁷ (III)

wherein R⁷ is $$-\overset{O}{\underset{}{C}}R^3, \ -\overset{O}{\underset{}{C}}NR^4R^5,$$

or —SO$_2$R² and R² and R⁴ are as further defined directly hereinabove in the presence of an inert solvent and a hydrogen halide absorber (acid scavenger) to obtain the desired compound corresponding to the formula

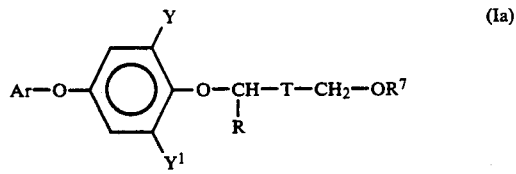

(Ia)

wherein in Formulae Ia, II and III; Ar, Y, Y¹, R, R⁷ and T are as hereinabove defined and hal- is chloro or bromo.

The reaction is generally carried out at a temperature in the range of from about 0° to about 25° C.

While not normally necessary, a catalyst can be employed, if desired. Representative catalysts include, for example, 4-dimethylaminopyridine and 1,4-diazabicyclo-2,2,2-octane.

Representative inert solvents for this reaction include, for example, chlorinated hydrocarbons (for example, methylene chloride), ether, toluene, pyridine, hexane, acetonitrile and the like.

Representative hydrogen halide absorbers include tertiary amines, alkali metal hydroxides and alkali metal carbonates. Additionally, when pyridine is employed as the solvent, it can also function as the hydrogen halide absorber.

The compounds of the present invention wherein R¹ is

and R³ is other than —NR⁴R⁵ can be prepared by the reaction of an appropriate alkenol corresponding to Formula II with an ester corresponding to the formula

(IIIa)

wherein R, L and R³ are as hereinabove defined. This reaction can be carried out employing the same solvents and conditions as set forth hereinabove for the reaction between the reactants of Formulae II and III.

Additionally, when, $R^1$ is

and $R^3$ is other than $-NR^4R^5$ an appropriate anhydride corresponding to the formula wherein $R^3$ is as hereinbefore defined can be reacted with the alkenol or thiol corresponding to Formula II

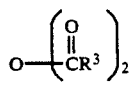    (IV)

employing the same solvents and conditions as set forth hereinabove for the reaction between the reactants of Formulae II and III.

The specific reaction times employed in the hereinabove and hereinafter set forth preparative procedures vary considerably and are dependent upon factors such as the solvent, base, catalyst, if employed, reaction temperature and the reactivity of the specific reactants employed. The reactions are for the most part complete in a period of from about 30 minutes to about 12 hours or more.

The above-indicated active compounds of the present invention can be prepared in an alternative procedure by the reaction of substantially equimolar amounts of a compound of Formula II with a strong alkali base such as sodium hydride or the like to irreversibly abstract the hydrogen proton followed by the direct treatment of the resulting alkali metal alkoxide material without separation, with an acid halide of Formula III.

The compounds of the present invention wherein $R^1$ is

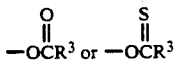

and $R^3$ is $-NHR^5$ can be prepared by the condensation of an appropriate alkenol of Formula II with an appropriate isocyanate or isothiocyanate corresponding to the formula $$R^5NC=L \quad (V)$$

wherein L and $R^5$ are as hereinbefore defined. The reaction is generally carried out in the presence of an inert solvent such as methylene chloride or toluene at ambient temperatures, though the use of higher temperatures could be necessary depending on the $L=CNR^5$ reactant to effect condensation. A catalytic amount of a base such as, for example, triethylamine, is sometimes beneficial. The isocyanate and isothiocyanate reactants are all known compounds of commerce.

The compounds of the present invention which correspond to the formula

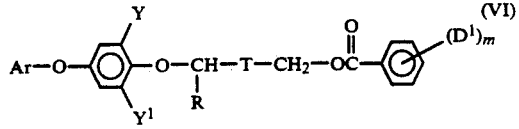    (VI)

wherein Ar, Y, $Y^1$, R, T and m are as hereinbefore set forth and $D^1$ is

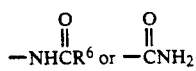

and $R^6$ is as hereinbefore defined, can be prepared by the reaction, at ambient temperature, of an appropriate 4-((aryloxy)phenoxy)-alkenol corresponding to the formula

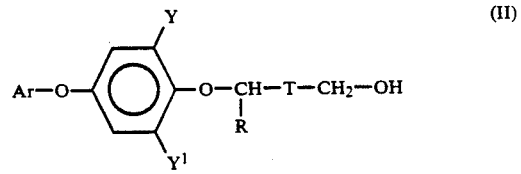    (II)

wherein Ar, Y, $Y^1$, R and T are as hereinbefore set forth with an appropriate substituted benzoic acid corresponding to the formula

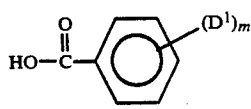    (VII)

wherein $D^1$ and m are as hereinbefore set forth in the presence of a solvent such as DMF, methylene chloride or ether and in the presence of a catalyst such as 4-(dimethylamino)pyridine and an aid for forming esters at low temperatures. Representative of such agents are carbodiimides such as dicyclohexylcarbodiimide.

The desired product can be separated from the reaction mixture of the above preparative procedures employing conventional separatory procedures known to those skilled in the art including steps of solvent extraction, filtration, water washing, column chromatography, neutralization, acidification, crystallization and distillation.

The preparation of the optical isomer forms of the active compounds of the present invention follow conventional procedures employed to prepare related compounds. Such procedures include those taught in U.S. patent application Ser. No. 4,532,328; European Patent Applications 2,800, 3,890 and 6,608; German OLS 2,949,728 and U.K. Patent Application GB 2,042,503A. The teachings of these applications are incorporated herein by reference thereto.

Since the hereinabove and hereinafter set forth compound preparation procedures employ only standard chemistry practices, and it is known that slightly different reactants can require slightly different reaction parameters from those for other reactants, it is to be understood that minor modifications to the reaction parameters set forth such as the use of an excess of one reactant, the use of a catalyst, the use of high temperature and/or pressure equipment, high speed mixing and other such conventional changes are within the scope of this invention.

Preparation of Starting Materials

The 4-((aryloxy)phenoxy)alkenols employed herein as starting materials and corresponding to the formula

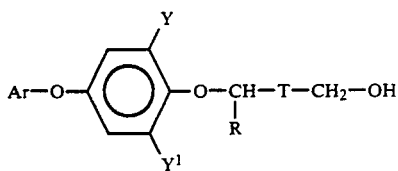

(II)

are for the most part known compounds and can be prepared employing known techniques including reducing carboxylic acids and their esters which correspond to the formula

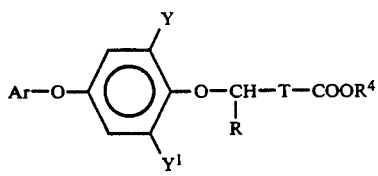

(VIII)

wherein in Formulae II or VIII; Ar, Y, $Y^1$, R, T and $R^4$ are as hereinbefore defined.

Representative compounds of Formula II can be found in U.S. Pat. Nos. 3,946,084; 4,267,317 and 4,360,375; European Patent Applications 10,232; 42,750; 46,467; 46,468 and 47,972; West German DE OF 2,926,607 and Chemical Abstracts 94:83960C wherein such compounds and their preparation are taught.

Representative compounds of Formula VIII can be found in U.S. Pat. Nos. 3,900,507; 4,163,661; 4,216,007; 4,263,040; 4,360,375 and 4,368,068; Japan Kokai 79-109,915; 81-43,269; 81-57,769; 81-63,968; 81-75,405 and 81-67,671; West German DE OF 2,926,607 and 2,948,095 and European Patent Applications 42,750; 46,467; 46,468 and 47,972 wherein such compounds and their preparations are taught.

Many of the compounds of Formulae II and VIII which are not specifically taught in the above-cited references can be prepared using the procedures of these references and employing the appropriate starting materials. These references are incorporated herein by reference thereto.

Additionally, the compounds of Formulae II and VIII can be prepared by the reaction of an appropriate arylhalide corresponding to the formula Ar—$X^1$    (IX)

wherein Ar is as hereinbefore defined and $X^1$ represents —Br, —Cl or —F and an appropriate hydroxyphenoxyalkenol or hydroxyphenoxy alkenyl carboxylic acid or ester corresponding to the formula

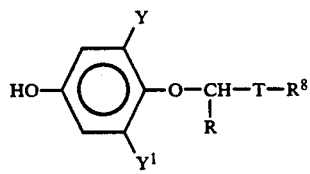

(X)

wherein Y, $Y^1$, R and T are as hereinbefore defined and $R^8$ is —CH$_2$OH or —COOR$^4$. In carrying out this reaction, the reactants and a strong base such as an anhydrous alkali metal hydride, alkoxide, hydroxide or carbonate are mixed together in a dipolar, aprotic solvent such as, for example, dimethylformamide (DMF), acetone, methyl ethyl ketone, acetonitrile, dimethylsulfoxide (DMSO), sulfolane, N-methylpyrrolidone or the like. The reaction is advantageously carried out at elevated temperatures of from about 50° to 120° C. This procedure is also the preferred procedure to use when Ar is quinoxalinyl or pyrimidinyl.

The compounds of Formulae II and VIII wherein Y and $Y^1$ are both hydrogen can also be prepared by the reaction of an appropriate aryloxyphenol corresponding to the formula

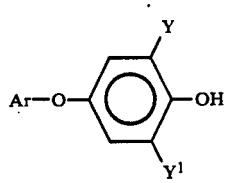

(XI)

with an appropriate α-haloalkenol or α-haloalkenoic acid or ester corresponding to the formula

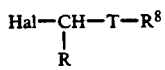

(XII)

wherein Ar, Y, $Y^1$, Hal, R, T and $R^8$ are as hereinbefore defined employing the same reaction conditions as set forth hereinabove for the reaction between the reactants of Formulae IX and X. This is not a preferred procedure to employ when Y and/or $Y^1$ are fluorine due to an increase in the number of isomers present during the preparation of the compound of Formula XI.

The hydroxyphenoxy alkenols, carboxylic acid or esters corresponding to the formula

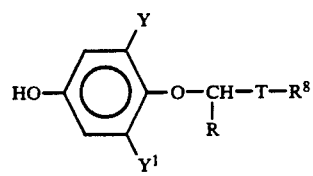

(X)

are prepared by a variety of procedures. Those compounds wherein Y and $Y^1$ are both hydrogen, are for the most part known compounds and are taught in U.S. Pat. Nos. 4,216,007; 4,267,317 and 4,368,068; European Patent Applications 3,890; 46,467 and 46,468; and Japanese Kokai 80-79,344; 81-59,725 and 81-59,718.

Those compounds wherein Y and/or $Y^1$ are fluorine can be prepared in a multistep procedure as follows:

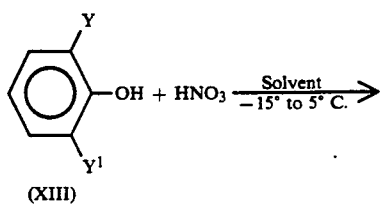

(XIII)

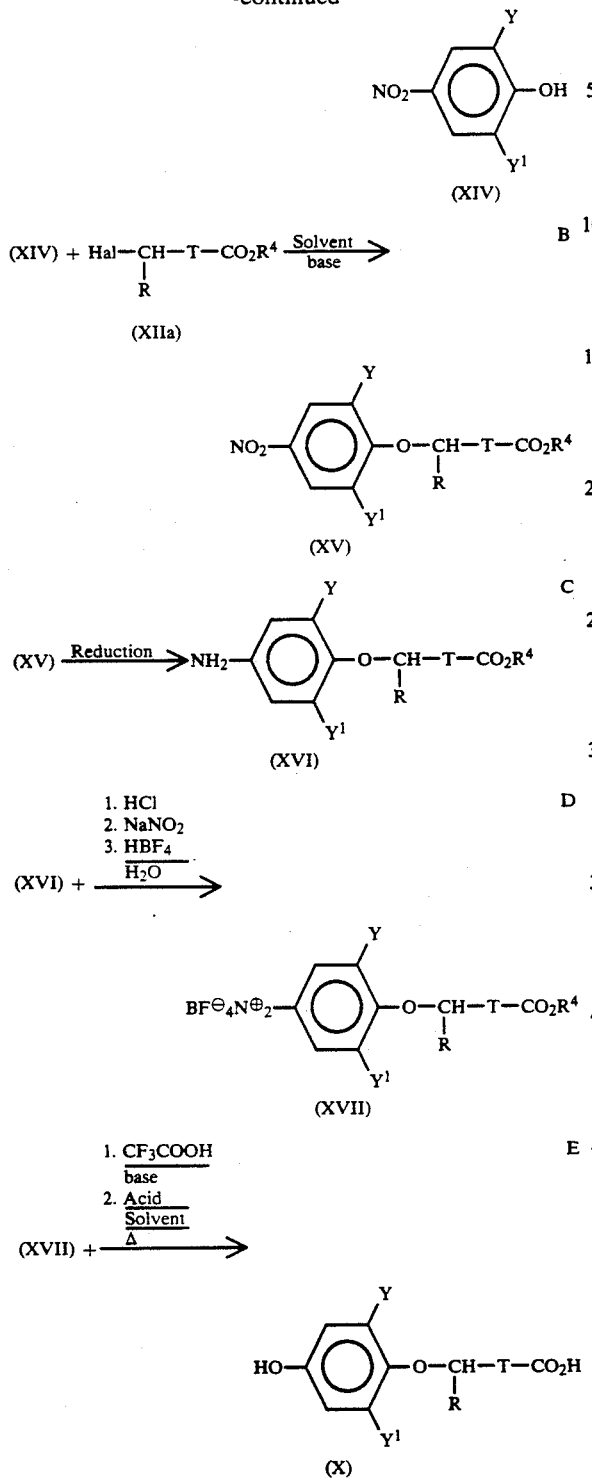

No attempt has been made to present a balanced equation in the above reaction sequence.

The above reaction steps can be carried out as follows:

Step A

The appropriate fluorophenol of Formula XIII in a solvent such as, for example, methylene chloride, is reacted for from about 1 to about 3 hours with 90 percent nitric acid at a temperature of from about $-15°$ C.

to about 5° C. At the end of this period, the desired 2-fluoro- or 2,6-difluoro-4-nitrophenol product of Formula XIV is recovered employing conventional procedures.

Step B

The thus formed 2-fluoro- or 2,6-difluoro-4-nitrophenol of Formula XIV is reacted with an appropriate α-haloalkenoic acid or ester corresponding to Formula XIIa. In carrying out this reaction, the phenol compound, the compound of Formula XIIa and a metallic base such as sodium or potassium carbonate, or an organic base such as triethylamine are mixed together in the presence of a solvent such as dimethylsulfoxide (DMSO), dimethylformamide, tetrahydrofuran, acetonitrile, hexamethylphosphoramide or N-methylpyrrolidone and heated to a temperature between about 40° C. to about 220° C. The desired fluorinated 4-nitrophenoxy alkenol, acid or ester corresponding to Formula XV is recovered employing conventional procedures.

Step C

The thus formed fluorinated 4-nitrophenoxyalkenoic, acid or ester corresponding to Formula XV is selectively reduced to the corresponding amino (aniline) compound corresponding to Formula XVI. This reduction can be conveniently carried out employing conventional stannous chloride reduction procedures. The product is recovered employing conventional recovery procedures.

Step D

The thus formed aniline compound corresponding to Formula XVI is treated with an aqueous solution of concentrated HCl at a temperature of from about 0°-10° C. and this solution is then reacted with an aqueous solution of sodium nitrite. This mixture is thereafter reacted with an aqueous solution of fluoroboric acid to form the desired corresponding diazonium tetrafluoroborate compound corresponding to Formula XVII. The product is separated employing conventional procedure.

Step E

The thus formed compound corresponding to Formula XVII is treated under reflux conditions with a mixture of an alkali metal trifluoroacetate in trifluoroacetic acid followed by conventional acidification (if the free acid form is desired) to obtain the desired compound corresponding to Formula X.

The halides employed as starting materials and corresponding to the formula $$Hal-R^7 \qquad (III)$$

wherein Hal and $R^7$ are as hereinbefore defined are for the most part known in the chemical literature and/or commercially produced compounds.

In addition, those compounds not specifically taught or produced can be prepared by procedures analogous to those employed to prepare the taught or produced compounds employing the appropriate starting materials.

The ester compounds corresponding to the formula

(IIIa)

are well known in the chemical literature.

The aromatic/heterocyclic halides employed as starting materials and which correspond to the formula

 (IX)

wherein Ar and $X^1$ are as hereinbefore defined, are all known and/or commercially produced compounds and for the most part are taught in the above-listed applications and/or patents which teach preparing compounds of Formulae II and VIII. In addition, compounds of Formula IX not specifically taught can be prepared by procedures analogous to those of the above references employing the appropriate starting materials.

The α-haloalkenoic acid or esters employed as starting materials and corresponding to the formula

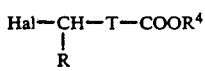 (XVIII)

wherein Hal, R, T and $R^4$ are as hereinbefore defined are all known compounds and such compounds are taught in U.S. Pat. Nos. 4,163,661; 4,216,007; 4,263,040 and 4,360,375 and European Patent Application 42,750, among others.

The following examples illustrate the present invention and the manner by which it can be practiced but, as such, are not to be construed as limitations upon the overall scope thereof.

The compounds obtained in the following examples were generally characterized by infrared and nuclear magnetic resonance spectrometry.

EXAMPLE 1

E isomer of 4-(4-hydroxyphenoxy)-2-penten-1-ol

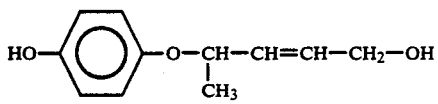

An oven-dried flask was equipped with a nitrogen inlet, a stirrer, a thermometer and a septum stoppered dropping funnel and was flushed with nitrogen. The flask was charged with a solution of 26.6 grams (g) (120 millimole (mmol)) of methyl (E)-4-(4-hydroxyphenoxy)-2-pentenoate in 150 milliliters (ml) of toluene. The solution was cooled to −78° C., and the dropping funnel was charged with 250 ml (375 mmol) of 25 percent (%) solution of diisobutylaluminum hydride (DIBAL) in toluene. The DIBAL solution was then added at −78° C. dropwise to the reaction mixture over a 1.5 hour period, and the reaction was stirred at −78° C. for an additional 0.5 hour. The reaction was quenched by cautious, dropwise addition of 250 ml of a stock solution prepared from 6 parts of water, 25 parts of acetic acid and 75 parts of ether while maintaining the temperature below −50° C. The resulting mixture was allowed to warm to room temperature and filtered, and the solid was washed with ether. The filtrates were combined and reserved while the solid was partitioned between water and ether.

This mixture was made acidic with aqueous HCl, and the ether layer separated and combined with the reserved filtrates. The combined organic solution was then washed to neutrality with saturated aqueous sodium bicarbonate, dried over MgSO$_4$ and evaporated to dryness. The oily residue was then purified by preparative scale liquid chromatography (HPLC) eluting with 3:2 hexane:acetone. Removal of solvent and thorough drying left 19.3 g (83%) of the desired alcohol as a tan oil.

| Elemental Analysis: | % C | % H |
|---|---|---|
| Calculated for $C_{11}H_{14}O_3$: | 68.02 | 7.26 |
| Found: | 67.24 | 7.26 |

EXAMPLE 2

E isomer of 4-(4-((6-chloro-2-quinolinyl)oxy)phenoxy)-2-penten-1-ol

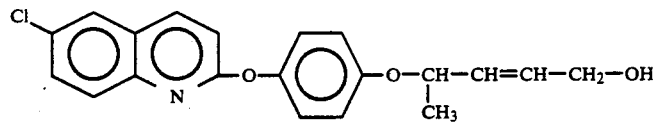

A mixture of 1.58 g (8 mmol) of 2,6-dichloroquinoline, 1.75 g (9 mmol) of (E)-4-(4-hydroxyphenoxy)-2-penten-1-ol, 1.52 g (11 mmol) of powdered, anhydrous potassium carbonate and 30 ml of dry dimethylsulfoxide was warmed under nitrogen at 110° C. for a period of 5 hours. The mixture was cooled to room temperature, poured into ice cold 1 percent aqueous sodium hydroxide, and the resulting aqueous mixture was extracted three times with ether. The combined ether layers were washed once with 1 percent aqueous sodium hydroxide and twice with water, dried over MgSO$_4$ and evaporated to dryness. The residue was purified by preparative scale HPLC, eluting with 7:3 hexane:ethyl acetate, and then thoroughly dried to leave 1.71 g (60%) of desired pentenol as a yellow, viscous gum.

EXAMPLE 3

E isomer of 4-(4-((6-chloro-2-quinoxalinyl)oxy)phenoxy)-2-penten-1-ol

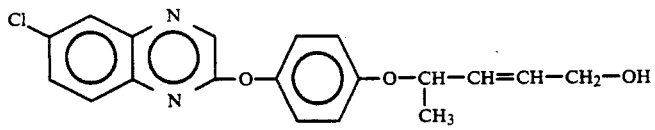

A mixture of 1.99 g (10 mmol) of 2,6-dichloroquinoxaline, 2.13 g (11 mmol) of (E)-4-(4-hydroxyphenoxy)-2-penten-1-ol, 1.73 g (12.5 mmol) of powdered, anhydrous potassium carbonate and 50 ml of dry acetonitrile was warmed at reflux under nitrogen for a period of 3 hours. The mixture was cooled to room temperature, and the solid filtered off and washed well with ether. The filtrates were combined and evaporated to dryness, and the residue partitioned between ether and 2 percent aqueous sodium hydroxide. The aqueous layer was separated and extracted again with ether. The combined organic layers were washed with water, dried over MgSO$_4$ and evaporated to dryness. The residual solid was purified by preparative scale HPLC, eluting with 7:3 hexane: ethyl acetate, to give a solid which was recrystallized from toluene. This gave 2.60 g (73%) of the desired pentenol as pale yellow crystals, having a melting point (m.p.) of 124°–126° C.

| Elemental Analysis: | % C | % H | % N |
|---|---|---|---|
| Calculated for C$_{19}$H$_{17}$ClN$_2$O$_3$: | 63.95 | 4.80 | 7.85 |
| Found: | 63.73 | 4.75 | 7.81 |

EXAMPLE 4

E isomer of 4-(4-((5-iodo-2-pyrimidinyl)oxy)phenoxy)-2-penten-1-ol

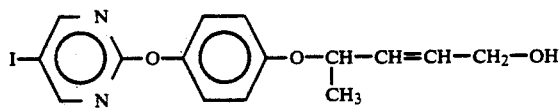

A mixture of 1.68 g (7 mmol) of 2-chloro-5-iodopyrimidine, 1.55 g (8 mmol) of (E)-4-(4-hydroxyphenoxy-2-penten-1-ol, 1.24 g (9 mmol) of powdered, anhydrous potassium carbonate and 35 ml of dry acetonitrile was stirred under nitrogen at reflux for a period of 3 hours. The mixture was cooled and filtered, and the filtered solid was thoroughly washed with ether. The filtrates were combined and evaporated to dryness, and the residue partitioned between ether and 1 percent aqueous sodium hydroxide. The aqueous layer was separated and again extracted with ether. The combined organic layers were washed twice with water, dried over MgSO$_4$ and evaporated to dryness. The residual oil was purified by preparative scale HPLC, and then dried in a Kugelrohr apparatus at 55° C. and 0.1 mm Hg for 1 hour. This left 2.75 g (quantitative) of the desired pentenol as a pale yellow, viscous gum.

| Elemental Analysis: | % C | % H | % N |
|---|---|---|---|
| Calculated for C$_{15}$H$_{15}$IN$_2$O$_3$: | 45.24 | 3.80 | 7.04 |
| Found: | 44.70 | 3.67 | 6.78 |

EXAMPLE 5

Step A E isomer of 4-(4-((3-chloro-5-(trifluoromethyl)-2-pyridinyl)oxy)phenoxy-2-pentenoic acid, methyl ester

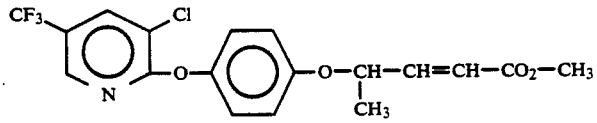

A mixture of 28.95 g (0.1 mol) of 4-((3-chloro-5-(trifluoromethyl)-2-pyridinyl)oxy)phenol, 16.56 g (0.12 mol) of powdered, anhydrous potassium carbonate and 250 ml of dry acetonitrile was warmed at reflux under nitrogen for 1.5 hours. The mixture was cooled to room temperature and 20.27 g (0.105 mol) of methyl (E)-4-bromo-2-pentenoate was added. The resulting mixture was maintained at reflux for 2.5 hours and then cooled to room temperature and filtered. The filtered solid was washed with ether, and the combined filtrates evaporated to dryness on a rotovap. The residual oil was taken up in ether, and the organic solution washed twice with water, twice with 5 percent aqueous sodium hydroxide solution and again with water, dried over MgSO$_4$ and evaporated on a rotovap. The residual solid was crystallized twice from hexane to give nearly colorless crystals of the desired pentenoate product. The filtrates from the recrystallization were combined and filtered through silica gel, eluting with CH$_2$Cl$_2$. Removal of solvent under vacuum left a colorless solid which was recrystallized from hexane to give additional pentenoate product. Total yield was 27.24 g (68%) of colorless crystals melting at 88°–90° C.

| Elemental Analysis: | % C | % H | % N |
|---|---|---|---|
| Calculated for C$_{18}$H$_{15}$ClF$_3$NO$_4$ | 53.81 | 3.76 | 3.49 |
| Found: | 53.65 | 3.49 | 3.43 |

Step B E isomer of 4-(4-((3-chloro-5-(trifluoromethyl)-2-pyridinyl)oxy)phenoxy)-2-penten-1-ol

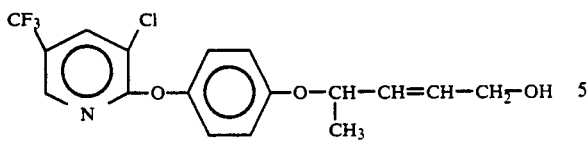

An oven-dried flask was equipped with a thermometer, a nitrogen inlet, a magnetic stirrer and a dropping funnel and flushed with nitrogen. The flask was charged with 20.08 g (0.05 mol) of (E)-4-(4((3-chloro-5-(trifluoromethyl)-2-pyridinyl)oxy)phenoxy-2-pentenoic acid, methyl ester and 150 ml of toluene, and the addition funnel was stoppered with a rubber septum The solution was cooled to −78° C., and the addition funnel charged with 70 ml (0.105 mol) of 25 percent diisobutylaluminumhydride (DIBAL) in toluene. The DIBAL was then added dropwise to the reaction solution at such a rate that the temperature remained <−60° C. Upon completion of the addition, the solution was maintained at −78° C. for 30 minutes, and then 70 ml of a stock solution prepared from 6 ml of water, 25 ml of glacial acetic acid and 75 ml of ether was placed in the dropping funnel and added dropwise over 30 minutes to the reaction mixture. The mixture was then allowed to warm to room temperature, and the alumina gel filtered off and washed well with ether. The combined filtrates were washed with dilute aqueous HCl, saturated aqueous sodium bicarbonate, dried over MgSO$_4$ and evaporated to dryness on a rotovap. The residual oil was purified by preparative scale HPLC, eluting with 7:3 hexane:ethyl acetate. The resulting nearly colorless viscous oil was dried on the rotovap at 65° C. and about 1 mm Hg vacuum for 1.5 hours. Total yield of the desired pentenol product was 16.41 g (88%).

| Elemental Analysis: | | | |
|---|---|---|---|
| | % C | % H | % N |
| Calculated for C$_{17}$H$_{15}$ClF$_3$NO$_3$ | 54.63 | 4.05 | 3.75 |
| Found: | 54.09 | 3.85 | 3.67 |

By following the procedures of Examples 1-4 (Method A) and Example 5 (Method B), employing the appropriate starting phenols, the following alkenols are prepared.

TABLE 6

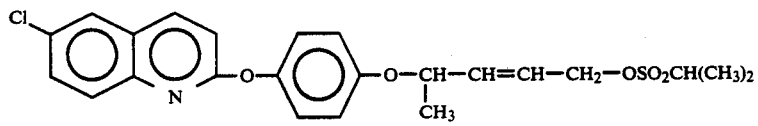

| Method | Ar | M.P. °C. | Molecular Formula and Elemental Analysis | | |
|---|---|---|---|---|---|
| | | | % C | % H | % N |
| A | (6-chloro-benzothiazolyl) | 94–97 | C$_{17}$H$_{15}$ClN$_2$O$_3$S Calc: 56.27 4.17 7.72 Found: 55.98 4.07 7.75 | | |

EXAMPLE 6

E isomer of 4-(4-((6-chloro-2-quinolinyl)oxy)phenoxy-2-penten-1-ol, 1-methylethylsulfonate

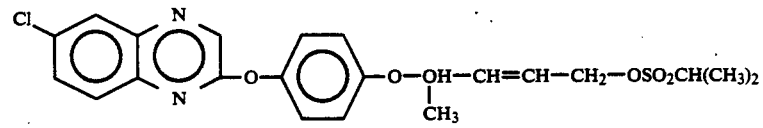

A solution prepared from 1.07 g (3 mmol) of the pentenol obtained in Example 2, 0.40 g (4 mmol) of triethylamine, and 20 ml of methylene chloride was cooled at 0° C. under nitrogen and a solution of 0.50 g (3.5 mmol) of isopropylsulfonylchloride in 3 ml of methylene chloride was added in one portion. The resulting solution was stirred at 0° C. for 30 minutes and then poured into a mixture of ether and about 1N aqueous HCl. The organic layer was separated, dried over MgSO$_4$ and evaporated to dryness. The residue was purified by preparative scale HPLC, eluting with 3:1 hexane:ethyl acetate, and then dried in a Kugelrohr apparatus at 50° C. and 0.1 mm Hg for 1 hour. This left 1.31 g (95%) of desired sulfonate product as a viscous oil. (Compound 1).

| Elemental Analysis: | | | |
|---|---|---|---|
| | % C | % H | % N |
| Calculated for C$_{23}$H$_{24}$ClNO$_5$S: | 59.80 | 5.24 | 3.03 |
| Found: | 58.91 | 5.11 | 2.90 |

EXAMPLE 7

E isomer of 4-(4-((6chloro-2-quinoxalinyl)oxy)-phenoxy)-2-penten-1-ol, 1-methylethyl sulfonate A solution prepared from 1.78 g (5 mmol) of the pentenol obtained in Example 3 above, 0.61 g (6 mmol) of triethylamine and 25 ml of methylene chloride was cooled under N$_2$ at 0° C. while 0.78 g (5.5 mmol) of isopropylsulfonylchloride was added in one portion.

After stirring at 0° C. for 45 minutes, the mixture was poured into a mixture of ether and water. The organic layer was separated, dried over MgSO4 and evaporated to dryness. The residual solid was taken up in boiling hexane, filtered while hot and allowed to cool to give pale yellow crystals. The crystals were filtered and dried to give 1.65 g (71%) of the desired sulfonate product, m p. 95°-96° C. (Compound 2).

| Elemental Analysis: | | | |
|---|---|---|---|
| | % C | % H | % N |
| Calculated for C22H23ClN2O5S: | 57.07 | 5.01 | 6.05 |
| Found: | 56.78 | 4.92 | 5.96 |

EXAMPLE 8

E isomer of 4-(4-((5-iodo-2-pyrimidinyl)oxy)phenoxy)-2-penten-1-ol, (1-methylethyl)sulfonate

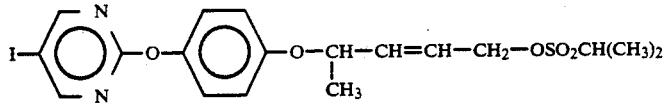

A solution prepared from 1.59 g (4 mmol) of the pentenol obtained in Example 4 above, 0.51 g (5 mmol) of triethylamine and 25 ml of methylene chloride was stirred under nitrogen at 0° C. while a solution of 0.63 g (4.4 mmol) of isopropylsulfonylchloride in 3 ml of methylene chloride was slowly added. The resulting solution was stirred at 0° C. for 1 hour and then poured into a mixture of ice cold 1N aqueous HCl and ether. The organic layer was separated, dried over MgSO4 and evaporated to dryness. The residual oil was purified by preparative scale HPLC, eluting with 3:1 hexane:ethyl acetate, and then dried in a Kugelrohr apparatus at about 0.2 mm Hg. This left 1.78 g (88%) of the desired sulfonate product as a straw-colored, viscous oil. (Compound 3).

| Elemental Analysis: | | | |
|---|---|---|---|
| | % C | % H | % N |
| Calculated for C18H17IN2O5S: | 42.86 | 4.20 | 5.56 |
| Found: | 42.01 | 4.11 | 5.26 |

EXAMPLE 9

E isomer of 4-(4-((3-chloro-5-(trifluoromethyl)-2-pyridinyl)oxy)-phenoxy)-2-penten-1-ol, methane sulfonate

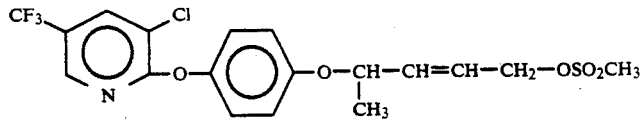

A solution prepared from 5.60 g (15 mmol) of (E)-4-(4-((3-chloro-5-(trifluoromethyl)-2-pyridinyl)oxy)-phenoxy)-2-penten-1-ol (prepared as in Step B of Example 5), 1.62 g (16 mmol) of triethylamine and 100 ml of methylene chloride was stirred at 0° C. under N2 while a solution of 1.83 g (16 mmol) of methane sulfonylchloride in 10 ml of methylene chloride was added in portions over 30 minutes. The resulting solution was stirred at 0° C. for 30 minutes and then at ambient temperature for 30 minutes and finally poured into ice cold 1N aqueous HCl. The organic layer was separated, dried over MgSO4 and evaporated to dryness. The residual oil was purified by preparative scale HPLC, eluting with 3:1 hexane:ethyl acetate, and then dried on a rotovap at 65° C. and about 1 mm Hg for 1.5 hours to give 5.82 g (85%) of desired product as a colorless viscous oil. Upon standing for one week in the hood, the oil solidified, and seed crystals were collected. The remaining material was taken up in a mixture of ethyl acetate and hexane, the seed crystals added and the mixture stirred. Colorless crystalline product precipitated and was filtered off and washed with hexane. The crystalline product melted at 64°-65° C. (Compound 4).

| Elemental Analysis: | | | |
|---|---|---|---|
| | % C | % H | % N |
| Calculated for C18H17ClF3NO5S: | 47.84 | 3.79 | 3.10 |
| Found: | 48.09 | 3.55 | 3.11 |

EXAMPLE 10

E isomer of 4-(4-((3-chloro-5-(trifluoromethyl)-2-pyridinyl)oxy)-phenoxy)-2-penten-1-ol, (1-methylethyl)sulfonate

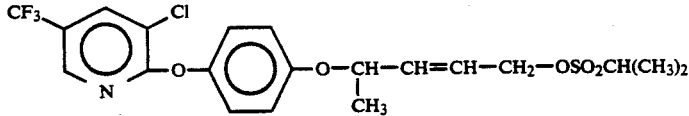

A solution of 2.24 g (6 mmol) of the pentenol obtained in Step B of Example 5, 0.71 g (7 mmol) of triethylamine and 50 ml of methylene chloride was stirred under N2 at 0° C. while a solution of 1.00 g (7 mmol) of isopropylsulfonylchloride in 3 ml of CH2Cl2 was added in portions. The solution was then allowed to warm slowly to 20° C. and then poured into a mixture of 1 percent aqueous HCl and ether. The aqueous layer was separated and extracted with ether. The combined organic layers were washed twice with water, dried over MgSO4 and evaporated to dryness. The residual oil was purified by preparative scale HPLC, eluting with 4:1 hexane:ethyl acetate, and then dried on the rotovap at 55° C. and about 1 mm Hg for 2 hours. This gave 2.39 g (83%) of desired product as a colorless, viscous gum. (Compound 5).

| Elemental Analysis. | | | |
|---|---|---|---|
| | % C | % H | % N |
| Calculated for C20H21ClF3NO5S: | 50.05 | 4.41 | 2.92 |
| Found: | 49.43 | 4.30 | 2.80 |

EXAMPLE 11

E isomer of 4-(4-((3-chloro-5-(trifluoromethyl)-2-pyridinyl)oxy)-phenoxy)-2-penten-1-ol, N-(1-methylethyl)sulfamate

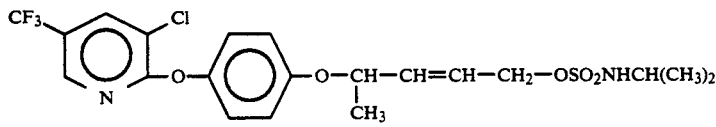

A solution prepared from 1.87 g (5 mmol) of the pentenol obtained in Step B of Example 5, 0.61 g (6 mmol) of triethylamine and 50 ml of methylene chloride was stirred at 0° C. under N2 while a solution of 0.87 g (5.5 mmol) of isopropylsulfamoyl chloride in 2 ml of methylene chloride was added in one portion. The resulting solution was stirred at 0° C. for 45 minutes and then poured into a mixture of ice cold 1N aqueous HCl and ether. The organic layer was separated, dried over MgSO4 and evaporated to dryness. The residual oil was purified by preparative scale HPLC, eluting with 3:1 hexane:ethyl acetate, and then dried in a Kugelrohr apparatus at 55° C. and 0.1–0.2 mm Hg for 1 hour. This left 2.35 g (95%) of desired sulfamate product as a pale yellow, viscous oil. (Compound 6).

| Elemental Analysis: | | | |
|---|---|---|---|
| | % C | % H | % N |
| Calculated for C20H22ClF3N2O5S: | 48.53 | 4.48 | 5.66 |
| Found: | 48.44 | 4.39 | 5.64 |

By following the procedure of Examples 6–12 employing the appropriate starting pentenols and sulfonyl or sulfamoyl halides, the following compounds in Table 7 are prepared.

TABLE 7

Ar—O—⟨benzene⟩—O—CH(CH3)—CH=CH—CH2—OSO2—R2

| Compound No. | Ar | R2 | M.P. °C. | Molecular Formula and Elemental Analysis |
|---|---|---|---|---|
| 7 | Cl-⟨pyridopyrazine⟩ | —NHCH(CH3)2 | 73–75 | C22H24ClN3O5S<br>Calc: 55.28 5.06 8.79<br>Found: 55.59 5.09 8.68 |
| 8 | Cl-⟨pyridopyrazine⟩ | —CH3 | 115–116 | C20H19ClN2O5S<br>Calc: 55.23 4.40 6.44<br>Found: 54.94 4.30 6.34 |
| 9 | Cl-⟨pyridopyrazine⟩ | —C2H5 | 95–97 | C21H21ClN2O5S<br>Calc: 56.18 4.72 6.24<br>Found: 56.27 4.58 6.14 |
| 10 | Cl-⟨pyridopyrazine⟩ | —C3H7 | 81–83 | C22H23ClN2O5S<br>Calc: 57.07 5.01 6.05<br>Found: 56.44 4.91 5.94 |
| | | | | C23H25ClN2O5S |

TABLE 7-continued

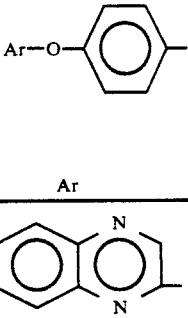

| Compound No. | Ar | R[2] | M.P. °C. | Molecular Formula and Elemental Analysis | | |
|---|---|---|---|---|---|---|
| | | | | % C | % H | % N |
| 11 | 6-chloro-quinoxalinyl | —C$_4$H$_9$ | 85–87 | Calc: 57.91 5.28 5.87 Found: 57.89 5.16 5.71 | | |

EXAMPLE 12

E isomer of 4-(4-((6-chloro-2-quinoxalinyl)oxy)phenoxy)-2-penten-1-ol, acetate

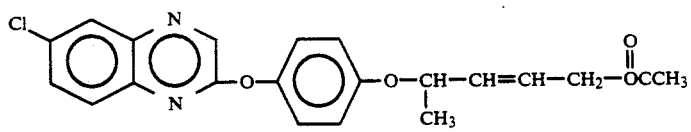

To an ice-cooled nitrogen flushed solution of 1.78 g (5 mmol) of the pentenol obtained, in Example 3 above in 10 ml of pyridine was added 0.61 g (6 mmol) of acetic anhydride. The resulting solution was allowed to warm to room temperature and stirred under nitrogen overnight. The solution was then poured into a mixture of ether and water. The organic layer was separated and washed three times with 2 percent aqueous HCl and saturated aqueous NaHCO$_3$, dried over MgSO$_4$ and evaporated to leave an off-white solid. The solid was purified by filtration, using methylene chloride as the solvent, through a short plug of silica gel, and then, after removal of solvent, recrystallized from methylcyclohexane. This gave colorless crystals which were filtered, washed with hexane and dried to give 1.27 g (64%) of the desired acetate as colorless crystals, m.p. 89°–90° C. (Compound 12).

Elemental Analysis:

| | % C | % H | % N |
|---|---|---|---|
| Calculated for C$_{21}$H$_{19}$ClN$_2$O$_4$: | 63.24 | 4.80 | 7.03 |
| Found: | 62.49 | 4.70 | 6.89 |

By following the procedures of Example 13 employing the appropriate starting pentenols and acid anhydride, the following compounds in Table 8 are prepared.

TABLE 8

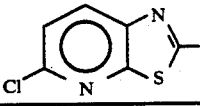

| Compound No. | Ar | Condition | Molecular Formula and Elemental Analysis | | |
|---|---|---|---|---|---|
| | | | % C | % H | % N |
| | | | C$_{19}$H$_{17}$ClN$_2$O$_4$S | | |
| 13 | 6-chloro-benzothiazolyl | thick gum | Calc: 56.36 4.23 6.92 Found: 55.96 4.20 7.29 | | |

EXAMPLE 13

E isomer of 4-(4-((6-chloro-2-quinoxalinyl)oxy)phenoxy)-2-penten-1-ol, benzoate

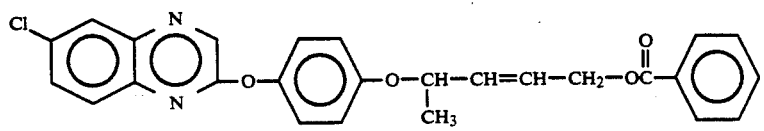

A nitrogen flushed solution of 1.78 g (5 mmol) of the pentenol obtained in Example 3 in 20 ml of pyridine was cooled in an ice bath and 0.77 g (5.5 mmol) of benzoylchloride was slowly added. The resulting mixture was stirred at 0° C. for 1 hour and then at ambient temperature for 2 hours. The reaction mixture was then poured into a mixture of water and ether. The organic layer was separated, washed twice with 1N aqueous HCl and then with saturated aqueous NaHCO3, dried over MgSO4 and evaporated to dryness. After standing at room temperature, the residue slowly crystallized and the solid recrystallized from methylcyclohexane to give, after filtering and drying, 1.90 g (82%) of the desired benzoate as colorless crystals melting at 79°-81° C. (Compound 14).

| Elemental Analysis: | % C | % H | % N |
|---|---|---|---|
| Calculated for $C_{26}H_{21}ClN_2O_4$: | 67.75 | 4.59 | 6.08 |
| Found: | 67.56 | 4.49 | 6.08 |

By substantially following the procedures of Example 14 employing the appropriate starting pentenols and acid halide in pyridine, the following compounds in Table 9 are prepared.

TABLE 9

$$Ar-O-\underset{}{\bigcirc}-O-CH-CH=CH-CH_2-O\overset{O}{\underset{\|}{C}}R^2$$
$$\phantom{Ar-O-\bigcirc-O-}|\phantom{CH=CH-CH_2-OCR^2}$$
$$\phantom{Ar-O-\bigcirc-O-}CH_3$$

| Compound No. | Ar | $R^2$ | M.P. °C. or Physical State | Molecular Formula and Elemental Analysis |
|---|---|---|---|---|
| 15 | 6-chloroquinoxalin-2-yl | $-C(CH_3)_3$ | 86–88 | $C_{24}H_{25}ClN_2O_4$<br>Calc: 65.37 5.72 6.35<br>Found: 65.39 5.72 6.28 |
| 16 | 5-chlorobenzothiazol-2-yl | phenyl | thick gum | $C_{24}H_{19}ClN_2O_4S$<br>Calc: 61.73 4.10 6.00<br>Found: 62.06 4.23 6.02 |
| 17 | 3-chloro-5-trifluoromethylpyridin-2-yl | phenyl | thick gum | $C_{24}H_{19}ClF_3NO_4$<br>Calc: 60.32 4.01 2.93<br>Found: 60.40 3.97 2.93 |
| 18 | 6-chloroquinoxalin-2-yl | 4-CF3-phenyl | 71–75 | $C_{27}H_{20}ClF_3N_2O_4$<br>Calc: 61.31 3.81 5.30<br>Found: 61.32 3.82 5.61 |
| 19 | 6-chloroquinoxalin-2-yl | $-CH(CH_3)_2$ | 45–49 | $C_{23}H_{23}ClN_2O_4$<br>Calc: 64.71 5.43 6.56<br>Found: 64.51 5.37 6.63 |
| 20 | 6-chloroquinoxalin-2-yl | $-C_3H_7$ | yellow oil | $C_{23}H_{23}ClN_2O_4$<br>Calc: 64.71 5.43 6.56<br>Found: 64.55 5.46 6.76 |
| 21 | 6-chloroquinoxalin-2-yl | 4-OCF3-phenyl | 80–84 | $C_{27}H_{20}ClF_3N_2O_5$<br>Calc: 59.51 3.70 5.14<br>Found: 59.10 3.68 5.29 |
| 22 | 6-chloroquinoxalin-2-yl | 4-CF3-phenyl | 70–74 | $C_{27}H_{23}ClN_2O_4$<br>Calc: 68.28 4.88 5.90<br>Found: 68.63 5.04 5.50 |
| 23 | 6-chloroquinoxalin-2-yl | 4-C2H5-phenyl | 87–89 | $C_{28}H_{25}ClN_2O_4$<br>Calc: 68.78 5.15 5.73<br>Found: 68.59 5.20 5.92 |

TABLE 9-continued

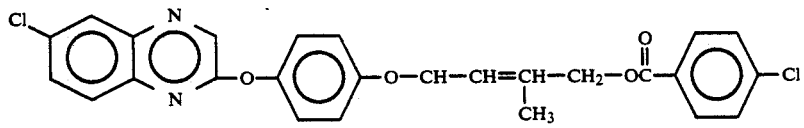

| Compound No. | Ar | R² | M.P. °C. or Physical State | Molecular Formula and Elemental Analysis %C %H %N |
|---|---|---|---|---|
| 24 | 6-chloro-quinoxalinyl | 4-nitrophenyl | 99–103 | C₂₆H₂₀ClN₃O₆<br>Calc: 61.73 3.98 8.31<br>Found: 62.13 4.11 8.28 |

EXAMPLE 14

E isomer of
4-(4-((6-chloro-2-quinoxalinyl)oxy)phenoxy)-2-penten-1-ol, 4-chlorobenzoate A nitrogen flushed solution of 1.78 g (5 mmol) of the pentenol obtained in Example 3 above, 0.61 g (6 mmol) of triethylamine and 40 ml of methylene chloride was cooled in an ice bath. A solution of 1.05 g (6 mmol) of 4-chlorobenzoyl chloride in 2 ml of methylene chloride was slowly added, and the resulting solution allowed to stir at ambient temperature overnight. The mixture was then poured into water, and the organic layer separated and washed with saturated aqueous NaHCO₃ and saturated aqueous NaCl, dried over MgSO₄ and evaporated to leave an oil. The oil was purified by preparative scale HPLC, eluting with 85:15 hexane:ethyl acetate. After removal of the solvent, an oil was obtained which, after trituration with hexane, solidified. The solid was filtered, washed with hexane and dried to give 1.91 g (77%) of the desired ester melting at 96°–99° C. (Compound 25).

| Elemental Analysis: | %C | %H | %N |
|---|---|---|---|
| Calculated for C₂₆H₂₀Cl₂N₂O₄: | 63.04 | 4.07 | 5.66 |
| Found: | 62.41 | 3.99 | 5.71 |

By following the procedures of Example 15 employing the appropriate starting pentenols and acid chloride, the following compounds in Table 10 are prepared.

TABLE 10

| Compound No. | Ar | R² | M.P. °C. or Physical State | Molecular Formula and Elemental Analysis %C %H %N |
|---|---|---|---|---|
| 26 | 6-chloro-quinoxalinyl | 2-chlorophenyl | 63–65 | C₂₆H₂₀Cl₂N₂O₄<br>Calc: 63.04 4.07 5.66<br>Found: 62.53 4.07 5.64 |
| 27 | 6-chloro-quinoxalinyl | 3-chlorophenyl | thick gum | C₂₆H₂₀Cl₂N₂O₄<br>Calc: 63.04 4.07 5.66<br>Found: 62.12 3.90 5.52 |

TABLE 10-continued

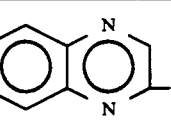

| Compound No. | Ar | R² | M.P. °C. or Physical State | Molecular Formula and Elemental Analysis |||
|---|---|---|---|---|---|---|
| | | | | % C | % H | % N |
| 28 | [6-chloroquinoxalinyl] | [2,6-dichlorophenyl] | 107-110 | C₂₆H₁₉Cl₃N₂O₄ Calc: 58.94 3.61 5.29 Found: 58.83 3.53 5.11 | | |

EXAMPLE 15

4-(Aminocarbonyl)benzoic acid, 4-(4-((6-chloro-2-quinoxalinyl)oxy)phenoxy)-2-pentenyl ester

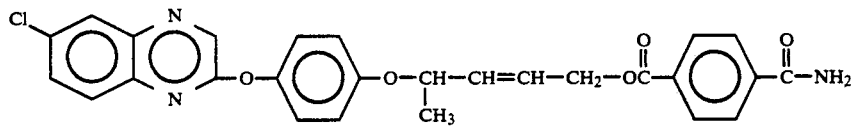

A mixture of 1.5 g (4.2 mmol) of the pentenol obtained in Example 3 above, 1.04 g (6.3 mmol) of 4-(aminocarbonyl)benzoic acid, 1.30 g (6.3 mmol) of dicyclohexylcarbodiimide (DCC), 0.05 g of 4-(dimethylamino)pyridine and 20 ml of DMF was stirred at room temperature overnight. An additional 0.3 g of DCC and 0.25 g of 4-(aminocarbonyl)benzoic acid were added and the mixture was stirred an additional 20 hours. The mixture was then poured into ether, water added and filtered. The filtrates were separated, and the organic layer washed with saturated aqueous NaHCO₃ and water, dried over MgSO₄ and evaporated to dryness. The residue was purified by preparative scale HPLC, eluting with a 3:2 hexane:acetone mixture to give 0.55 g of the desired product as a tan, glassy solid, m.p. 144°-148° C. (Compound 29).

| Elemental Analysis: | % C | % H | % N |
|---|---|---|---|
| Calculated for C₂₇H₂₂ClN₃O₅: | 64.35 | 4.40 | 8.34 |
| Found: | 63.97 | 4.70 | 8.06 |

EXAMPLE 16

4-(Acetylamino)benzoic acid, 4-(4-((6-chloro-2-quinoxalinyl)oxy)phenoxy)-2-pentenyl ester

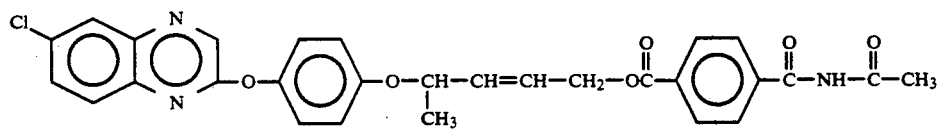

A mixture of 1.5 g (4.2 mmol) of the pentenol obtained in Example 3 above, 0.82 g (4.6 mmol) of 4-(acetylamino)benzoic acid, 0.95 g (4.6 mmol) of dicyclohexylcarbodiimide and 0.05 g of 4-(dimethylamino)-pyridine in 20 ml of dimethylformamide was stirred at room temperature for 72 hours. The mixture was diluted with ether and water and filtered. The filtrates were separated, and the organic layer washed with saturated aqueous NaHCO₃ and water, dried over MgSO₄ and evaporated to dryness. The residue was purified by preparative scale HPLC, eluting with a 65:35 hexane:acetone mixture to give 0.6 g of the desired product as a pale yellow, glassy solid, m.p. 62°-68° C. (Compound 30).

| Elemental Analysis: | % C | % H | % N |
|---|---|---|---|
| Calculated for C₂₈H₂₄ClN₃O₅: | 64.93 | 4.67 | 8.11 |
| Found: | 64.48 | 5.01 | 8.27 |

EXAMPLE 17

4-(4-((6-Chloro-2-quinoxalinyl)oxy)phenoxy)-2-penten-1-ol, methylcarbamate

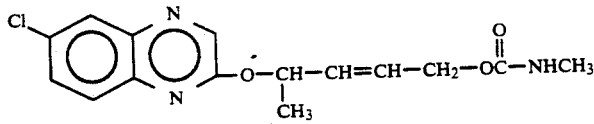

To a solution of 1.78 g (5 mmol) of the pentenol obtained in Example 3 above, was added 3 drops of triethylamine, 0.86 g (15 mmol) of methylisocyanate and 50 ml of methylene chloride. The solution was stirred at room temperature for 8 days. The solvent was separated and the residue was recrystallized twice from methylcyclohexane to give 1.68 g (81%) of the desired carbamate product as colorless crystals. The product melted at 114°–115° C. (Compound 31).

| Elemental Analysis: | | | |
|---|---|---|---|
| | % C | % H | % N |
| Calculated for $C_{21}H_{20}ClN_3O_4$: | 60.97 | 4.87 | 10.15 |
| Found: | 60.69 | 4.81 | 10.43 |

The compounds of the present invention have been found to be suitable for use in methods for the selective postemergent control of many annual and perennial grassy weeds in the presence of corn plants. It is to be noted that not all compounds will have the same effect on all weed plants. Some compounds will be more active in the control of one weed specie than another.

For such uses, unmodified active ingredients of the present invention can be employed. However, the present invention also embraces the use of the active compounds in admixture with inert materials, known in the art as agricultural adjuvants and/or carriers, in solid or liquid form. Thus, for example, an active ingredient can be dispersed on a finely-divided solid and employed therein as a dust or granule. Also, the active ingredients, as liquid concentrates or solid compositions comprising one or more of the active ingredients can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents. Suitable adjuvants of the foregoing type are well known to those skilled in the art.

The herbicidally effective concentration of the active ingredients in solid or liquid compositions generally is from about 0.0003 to about 95 percent by weight or more. Concentrations from about 0.05 to about 50 percent by weight are often employed. In compositions to be employed as concentrates, the active ingredient can be present in a concentration from about 5 to about 98 weight percent. The active ingredient compositions can also contain other compatible additaments, for example, phytotoxicants, plant growth regulants and other biologically active compounds used in agriculture.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as foxtail, barnyard grass, wild oats, Johnson grass and crabgrass while showing high selectivity to corn plants. These compounds are also uniquely effective in controlling perennial grassy weeds such as Johnson grass, quackgrass, and bermuda grass.

The exact amount of the active material to be applied is dependent not only on the specific active ingredient being applied, but also on the particular action desired, the weed plant species to be controlled and the stage of growth thereof as well as the part of the plant to be contacted with the toxic active ingredient. Thus, all of the active ingredients of the present invention and compositions containing the same may not be equally effective at similar concentrations or against the same weed plant species.

In the present postemergent operations, a dosage of about 0.01 to about 20 lbs/acre (0.056–22.4 kg/hectare) is generally applicable, although not all compounds are equally effective and some weeds are more difficult to control. Thus, a dosage rate in the range of about 0.05 to about 1.0 lb/acre (0.01–1.12 kg/hectare) is preferred in postemergent control of annual grassy weeds, while about 0.05 to about 5 lbs/acre (0.056–5.6 kg/hectare) is a preferred dosage range for the postemergent control of perennial grassy weeds. In applications to corn plants a weed controlling but less than corn plant damaging amount of from about 0.005 to about 1.0 lb/acre (0.0056 to 1.12 kgs/hectare) is generally employed.

The following examples illustrate the effects of the compounds of this invention.

EXAMPLE 18

Representative compositions of the present invention were evaluated to determine their effectiveness in postemergent operations.

Aqueous dispersions were prepared by admixing predetermined amounts of one of the hereinafter set forth compounds, dissolved in a predetermined amount of an inert solvent with a predetermined quantity of water and a predetermined amount of a surfactant to give aqueous dispersions of one of compounds 1–26 as the sole toxicant.

Seeds of various plant species were planted in beds of good agricultural soil and grown in a greenhouse. After the plants had emerged and had grown to a height of from 2-8 inches (depending on the plant species), separate beds of the plants were sprayed to runoff with one of the above-prepared compositions at a predetermined treating rate (in parts of the active compound per million parts of the ultimate composition (PPM)). Other beds of the plants were sprayed with a water-surfactant mixture, containing no active compound, to serve as controls. After treatment, the beds were maintained for two weeks under greenhouse conditions conducive for good plant growth. At the end of this period, the beds were examined to determine the amount of kill and control. The specific plant species, test compounds and the percent postemergent control are set forth below in Table 11.

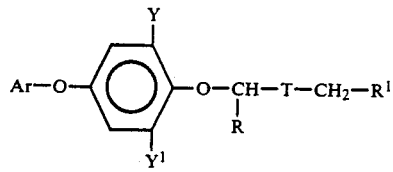

wherein Ar represents

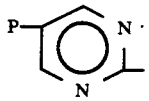

TABLE 11

| Compound No. Tested | Treatment Rate in PPM | Percent Kill and Control of the Following Plant Species | | | | |
|---|---|---|---|---|---|---|
| | | Corn | Crabgrass | Johnson Grass | Giant Foxtail | Green Foxtail |
| 1 | 1000 | 0 | NT | 90 | 85 | 90 |
|  | 500 | 0 | NT | 75 | 85 | 80 |
| 2 | 500 | 0 | 100 | NT | 100 | 100 |
|  | 250 | 0 | 100 | NT | 100 | 100 |
| 3 | 1000 | 0 | NT | 40 | 90 | 85 |
|  | 500 | 0 | NT | 10 | 90 | 80 |
| 4 | 125 | 60 | NT | 100 | 100 | 100 |
|  | 62 | 20 | NT | 90 | 100 | 80 |
| 5 | 125 | 20 | NT | 100 | 100 | 100 |
|  | 62 | 0 | NT | 100 | 100 | 100 |
| 6 | 125 | 20 | NT | 100 | 100 | 100 |
|  | 62 | 0 | NT | 90 | 90 | 100 |
| 7 | 250 | 0 | NT | 100 | 100 | 100 |
|  | 125 | 0 | NT | 100 | 100 | 100 |
| 8 | 500 | 0 | 80 | NT | 98 | 98 |
|  | 250 | 0 | 80 | NT | 100 | 98 |
| 9 | 500 | 0 | 100 | NT | 100 | 100 |
|  | 250 | 0 | 100 | NT | 100 | 100 |
| 10 | 500 | 0 | 98 | NT | 100 | 100 |
|  | 250 | 0 | 70 | NT | 98 | 100 |
| 11 | 500 | 0 | 95 | NT | 100 | 98 |
|  | 250 | 0 | 90 | NT | 100 | 98 |
| 12 | 500 | 0 | 100 | NT | 100 | 100 |
|  | 250 | 0 | 100 | NT | 100 | 100 |
| 13 | 125 | 0 | NT | NT | 95 | NT |
|  | 62 | 0 | NT | NT | 90 | NT |
| 14 | 500 | 10 | NT | 100 | 100 | 100 |
|  | 250 | 0 | NT | 100 | 100 | 100 |
| 15 | 500 | 20 | NT | 100 | 100 | 100 |
|  | 250 | 0 | NT | 100 | 100 | 100 |
| 16 | 500 | 0 | NT | NT | 90 | NT |
|  | 250 | 0 | NT | NT | 95 | NT |
| 17 | 250 | 10 | NT | 100 | 100 | 100 |
|  | 125 | 0 | NT | 100 | 60 | 100 |
| 18 | 62 | 10 | NT | 100 | 100 | 100 |
|  | 31 | 0 | NT | 80 | 90 | 20 |
| 19 | 125 | 20 | NT | 100 | 100 | 100 |
|  | 62 | 0 | NT | 100 | 100 | 100 |
| 20 | 500 | 10 | NT | 100 | 100 | 100 |
|  | 250 | 0 | NT | 100 | 100 | 100 |
| 21 | 250 | 20 | NT | 100 | 100 | 100 |
|  | 125 | 0 | NT | 100 | 90 | 50 |
| 22 | 500 | 20 | NT | 100 | 100 | 100 |
|  | 250 | 0 | NT | 100 | 100 | 100 |
| 23 | 250 | 20 | NT | 100 | 100 | 100 |
|  | 125 | 0 | NT | 100 | 90 | 95 |
| 24 | 250 | 0 | NT | NT | 94 | NT |
|  | 125 | 0 | NT | NT | 92 | NT |
| 25 | 250 | 5 | NT | NT | 90 | NT |
|  | 125 | 5 | NT | NT | 90 | NT |
| 26 | 250 | 5 | NT | NT | 98 | NT |
|  | 125 | 0 | NT | NT | 98 | NT |

What is claimed is:

1. A compound or an optical isomer thereof corresponding to the formula

Y and $Y^1$ each independently represent —H or —F;
R represents methyl or ethyl;
T represents T represents

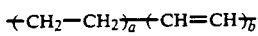

and the cis (Z) or trans (E) stereoisomers thereof or

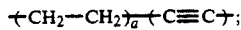

a represents the integer 0, 1 or 2;
b represents the integer 1 or 2;
P represents —Br, —Cl, —I or —CF$_3$;
R$^1$ represents —SO$_2$R$^2$,

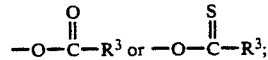

R$^2$ represents C$_1$-C$_4$ alkyl, C$_2$-C$_4$ alkenyl or —NR$^4$R$^5$;
R$^3$ represents C$_2$-C$_4$ alkenyl, C$_1$-C$_4$ alkyl, —NR$^4$R$^5$ or

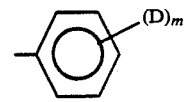

wherein
R$^4$ and R$^5$ each independently represent —H or C$_1$-C$_4$ alkyl;
D represents C$_1$-C$_4$-alkyl, —Br, —Cl, —NO$_2$, —CF$_3$, —OCF$_3$,

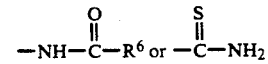

wherein R$^6$ represents C$_1$-C$_4$ alkyl and m represents an integer of from 0-3, inclusive.
2. A compound as defined in claim 1 which is in the R enantiomeric isomer form.
3. A compound as defined in claim 1 which is in the E stereoisomer form.
4. A compound as defined in claim 1 wherein P is —I.
5. A composition which comprises an agriculturally acceptable inert adjuvant in intimate admixture with a herbicidally effective amount of a compound, as the active material, which corresponds to the formula

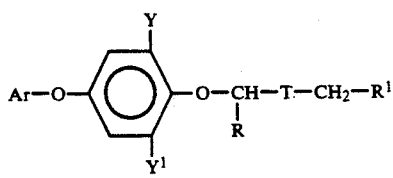

wherein Ar represents

Y and Y$^1$ each independently represent —H or —F;
R represents methyl or ethyl;

T represents

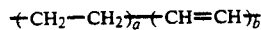

and the cis (Z) or trans (E) stereoisomers thereof or
a represents the integer 0, 1 or 2;
b represents the integer 1 or 2;
P represents —Br, —Cl, —I or —CF$_3$;
R$^1$ represents —SO$_2$R$^2$,

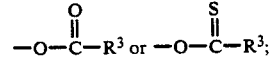

R$^2$ represents C$_1$-C$_4$ alkyl, C$_2$-C$_4$ alkenyl or —NR$^4$R$^5$;
R$^3$ represents C$_2$-C$_4$ alkenyl, C$_1$-C$_4$ alkyl, —NR$^4$R$^5$ or

wherein
R$^4$ and R$^5$ each independently represents —H or C$_1$-C$_4$ alkyl;
D represents C$_1$-C$_4$-alkyl, —Br, —Cl, —NO$_2$, —CF$_3$, —OCF$_3$,

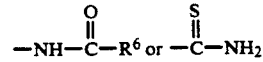

wherein R$^6$ represents C$_1$-C$_4$ alkyl and m represents an integer of from 0-3, inclusive.
6. A composition as defined in claim 5 wherein the compound is in the R enantiomeric isomer form.
7. A composition as defined in claim 5 wherein the compound is in the E stereoisomer form.
8. A composition as defined in claim 5 wherein P is —I.
9. A method for the postemergent kill and control of grassy weeds which comprises applying to said weeds a herbicidally effective amount of a composition comprising an agriculturally acceptable inert adjuvant in intimate admixture with, as the active material, a compound corresponding to the formula

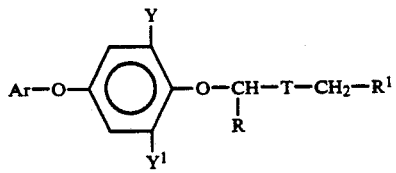

wherein Ar represents

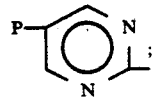

Y and Y$^1$ each independently represent —H or —F;
R represents methyl or ethyl;
T represents

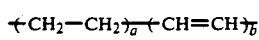

and the cis (Z) or trans (E) stereoisomers thereof or

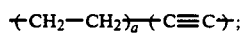

a represents the integer 0, 1 or 2;
b represents the integer 1 or 2;
P represents —Br, —Cl, —I or —CF$_3$;
R$^1$ represents —SO$_2$R$^2$,

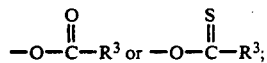

R$^2$ represents C$_1$-C$_4$ alkyl, C$_2$-C$_4$ alkenyl or —NR$^4$R$^5$;
R$^3$ represents C$_2$-C$_4$ alkenyl, C$_1$-C$_4$ alkyl, —NR$^4$R$^5$ or

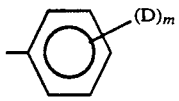

wherein
R$^4$ and R$^5$ each independently represent —H or C$_1$-C$_4$ alkyl;
D represents C$_1$-C$_4$-alkyl, —Br, —Cl, —NO$_2$, —CF$_3$, —OCF$_3$,

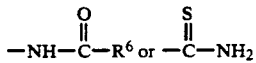

wherein R$^6$ represents C$_1$-C$_4$ alkyl and m represents an integer of from 0-3, inclusive.

10. A method as defined in claim 9 wherein the grassy weeds are selectively killed and controlled in the presence of corn plants.

11. A method as defined in claim 10 which is in the R enantiomeric isomer form.

12. A method as defined in claim 10 which is in the E stereoisomer form.

13. A method as defined in claim 10 wherein P is —I.

* * * * *